US00PP16348P2

(12) United States Plant Patent
Olesen

(10) Patent No.: US PP16,348 P2
(45) Date of Patent: Mar. 14, 2006

(54) MINIATURE ROSE PLANT NAMED 'POULPAH025'

(50) Latin Name: ***Rosa* hybrid**
Varietal Denomination: Poulpah025

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 44 days.

(21) Appl. No.: 11/001,950

(22) Filed: Dec. 1, 2004

(51) Int. Cl.
*A01H 5/00* (2006.01)

(52) U.S. Cl. ..... Plt./117

(58) Field of Classification Search ..... Plt./117, Plt./116

See application file for complete search history.

*Primary Examiner*—Anne Marie Grunberg
*Assistant Examiner*—June Hwu

(57) ABSTRACT

A new miniature rose plant which has abundant, white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpah025'.

The present invention constitutes a new and distinct variety of rose plant which originated from a controlled crossing between the female seed parent, an unnamed seedling, and the male pollen parent 'KORmutric' an unpatented variety. The two parents were crossed and the resulting seeds were planted in a controlled environment. The new variety is named 'Poulpah025'.

The new rose may be distinguished from the seed parent by the following combination of characteristics:

1. The seed parent has a general tonality of flower color of Yellow-Orange while 'Poulpah025' is White.
2. 'Poulpah025' has a very compact growth habit, while the seed parent is taller and less compact.

The new variety may be distinguished from its pollen parent, 'KORmutric' by the following combination of characteristics:

1. 'KORmutric' has 25 to 30 petals, whereas 'Poulpah025' has 140 petals.
2. Upper surface of interior petals on 'KORmutric' are Yellow Group 16C while the same on 'Poulpah025' are Green-White Group 157A.
3. Petal color as sepals unfold is Orange-White Group 159C for 'KORmutric'. Petal color as sepals unfold on 'Poulpah025' is Yellow-Green Group 145D.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'Poulpah025' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpah025' was selected by the inventor as a single plant from the progeny of the hybridization work done in June 2001. Asexual reproduction of 'Poulpah025' by cuttings and traditional budding was first done by Mogens N. Olesen in the nursery in Fredensborg, Denmark in July 2001. This initial and other subsequent propagations conducted in controlled environments have demonstrated that the characteristics of 'Poulpah025' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems of 'Poulpah025'. Specifically illustrated in FIG. 1:

FIG. 1.1; Flower bud, partially opened buds, and open bloom;

FIG. 1.2; Open flower, above view;

FIG. 1.3; Sepals, receptacle, and pedicel;

FIG. 1.4; Juvenile leaves exhibiting Anthocyanin;

FIG. 1.5; Flower petals, detached;

FIG. 1.6; Mature leaves.

DETAILED DESCRIPTION OF THE VARIETY

The following is a description of 'Poulpah025', as observed in its growth in glasshouses in Odense, Denmark in August 2004. Observed plants are 4 months of age and were cultivated in 15 cm pots. Color references are made using The Royal Horticultural Society (London, England) Colour Chart, 1995, except where common terms of color are used.

For a comparison, several physical characteristics of the rose variety 'Poulhi012', a rose variety from the same inventors described and illustrated in U.S. Plant Pat. No. 14,742 issued Apr. 27, 2004, are compared to 'Poulpah025' in Chart 1.

CHART 1

| | 'Poulpah025' | 'Poulhi012' |
|---|---|---|
| Petal Count. | 140. | 75 to 80 petals. |
| Fragrance. | Light floral scent. | None. |
| Flower diameter. | 65 mm. | 55 mm. |

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Ovate.

*Bud color.*—As sepals unfold, petals are Yellow-Green Group 145D.

*Sepals.*—Shape: Sepal apex is cirrhose. Base is flat at union with receptacle. Margin: Margins have strong foliaceous appendages and stipitate glands. Size: 25 to 35 mm (l)×7 to 10 mm (w). Variations: As flowers reach maturity sepals enlarge and foliaceous appendages become more distinct. Inner surface: Color: Yellow-Green Group 147A. Surface: Weakly pubescent. Outer surface: Color: Yellow-Green Group 146A. Texture: Smooth with very light pubescence.

*Receptacle.*—Surface: Smooth. Shape: Urn-Shaped. Size: 7 mm (h)×6 mm (w). Color: Yellow Green Group 144B.

*Pedicel.*—Surface: Somewhat rough with stipitate glands. Length: 30 mm average length. Diameter: 3.5 mm on average. Color: Yellow-Green Group 144B. No anthocyanin observed. Strength: Strong.

*Borne.*—Normally, flowers occur singularly.

Flower bloom:

*Fragrance.*—Fresh, floral scent.

*Duration.*—The blooms have a duration on the plant of approximately 28 days.

*Size.*—Flower diameter is 65 mm when open. Flower depth is 30 mm.

*Flower form.*—Very double, with many overlapping petals packed tightly into sections.

*Shape of flower, side view.*—Upon opening: Upper portion: Flat. Lower portion: Flat. After flowers opened: Upper portion: Flattened convex. Lower portion: Concave.

*Petalage.*—Under normal conditions, flowers have 140 petals total, 40 of which are petaloids.

*Flower petal color.*—Upon opening, outer petals Upper surface: White Group 155A to Yellow-Green Group 145D with intonations of Yellow-Green Group 144D. Lower surface: White Group 155A to Yellow-Green Group 145D with intonations of Yellow-Green Group 144D. Upon opening, inner petals: Upper surface: Green-White Group 157A. Lower surface: Green-White Group 157A with light intonations of Greyed-Red Group 182D at basal zone.

*Basal petal spots, upon opening.*—No distinctive coloration at the petal base observed.

*After opening, most outer petals.*—Upper surface: Green-White Group 157A with intonations of Yellow-Green Group 144D. Lower surface: Green-White Group 157A with intonations of Yellow-Green Group 144D.

*After opening, inner petals.*—Upper surface: White Group 155B. Lower surface: White Group 155B with light intonations of Greyed-Purple 182D at basal zone.

*Basal petal spots, after opening.*—No distinctive coloration at the petal base observed on innermost petals.

General tonality: On the open flower White Group 155A to 154D. No change in general tonality at the end of the 15$^{th}$ day. Afterwards general tonality is Yellow-White Group 158D.

Petals:

*Petal reflex.*—Double reflexation.

*Margin.*—Entire. Very strong undulations of margin observed on outer most guard petals. Inner petal margins have no undulations.

*Shape.*—Varying from broad elliptical to narrow elliptical. The apex is cuspidate. The base is obtuse.

*Size.*—Variable. Inner petals are 20 mm (l)×15 mm (w). Outer petals are 35 mm (l)×46 mm (w).

*Texture.*—Smooth.

*Thickness.*—Average.

Petaloids:

*Quantity.*—Normally 40.

*Shape.*—Elliptical.

*Color.*—White Group 155B on upper and lower surfaces.

*Size.*—13 mm (l)×5 mm (w).

Reproductive organs:

*Observations.*—Flowers appear to be sterile, with no distinctive reproductive organs.

*Petaloid stamens.*—Quantity: 20 to 30 normally. Color: White Group 155A with intonations of Greyed-Purple Group 182D.

*Hips.*—None observed.

PLANT

Plant growth: Moderate, upright to bushy. Average height of the plant is 25 to 30 cm. Average width is 20 to 25 cm.

Stems:

*Color.*—Juvenile growth is Yellow-Green Group 144A. Mature canes are Yellow-Green Group 144A.

*Length.*—On average, canes are 20 cm from the base of the plant to the flowering portion.

*Diameter.*—Normally 3 to 3.5 mm.

*Internodes.*—On mature canes, there is an average distance of 30 mm between nodes.

*Surface texture.*—Young wood: Smooth. Older wood: Smooth.

Thorns:

*Incidence.*—13 thorns per 10 cm of stem.

*Size.*—Average length of thorns on mature stems is 4 mm.

*Shape.*—Linear.

*Color.*—Mature and juvenile thorns are Greyed-Red Group 179C.

Plant foliage: Normal number of leaflets leaves in middle of the stem: 5 leaflets.

*Compound leaf.*—90 to 110 mm (l)×60 to 90 mm (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 144A with margins Greyed-Red Group 180A. Lower side: Yellow-Green Group 144B generalized with light intonations of Greyed-Red Group 180A.

Plant leaves and leaflets:

*Stipules.*—Size: 10 mm in length. Shape: Linear, slightly broad based with outward extending apecies. Margins: Finely serrated with few stipitate glands. Color: Yellow-Green Group 147A.

*Petiole.*—Length: 20 mm. Diameter: 1.5 mm.

*Upper surface.*—Color: Yellow-Green Group 144A. with Greyed-Purple Group 184A.

*Lower surface.*—Color: Yellow-Green Group 144B.

*Rachis.*—Length: 25 to 30 mm. Upper surface: Color: Yellow-Green Group 144A with Greyed-Purple Group 184A.

*Lower surface.*—Color: Yellow-Green Group 144B. Observations: Few stipitate glands and thorns observed.

*Leaflet.*—Edge: Doubly serrated. Size: Average size of the terminal leaflet on normal leaves is 43 to 52 mm (l)×27 to 30 mm (w). Shape: Ovate. Base shape: Obtuse. Apex shape: Pointed. Texture: Smooth. Thickness: Average to thin. Arrangement: Odd pinnate. Venation: Reticulate. Glossiness: Matte finish.

Disease resistance: Above average resistance to powdery and downy mildews, rust, black spot, and Botrytis under normal growing conditions in Fredensborg, Denmark.

Cold hardiness: The variety 'Poulpah025' has been found to be cold tolerant to USDA Cold Hardiness Zone 6.

It is claimed:

1. A new and distinct variety of rose plant named 'Poulpah025' substantially as illustrated and described herein as a distinct and novel rose variety due to its abundant white flowers, disease resistance, and extended period of bloom.

* * * * *

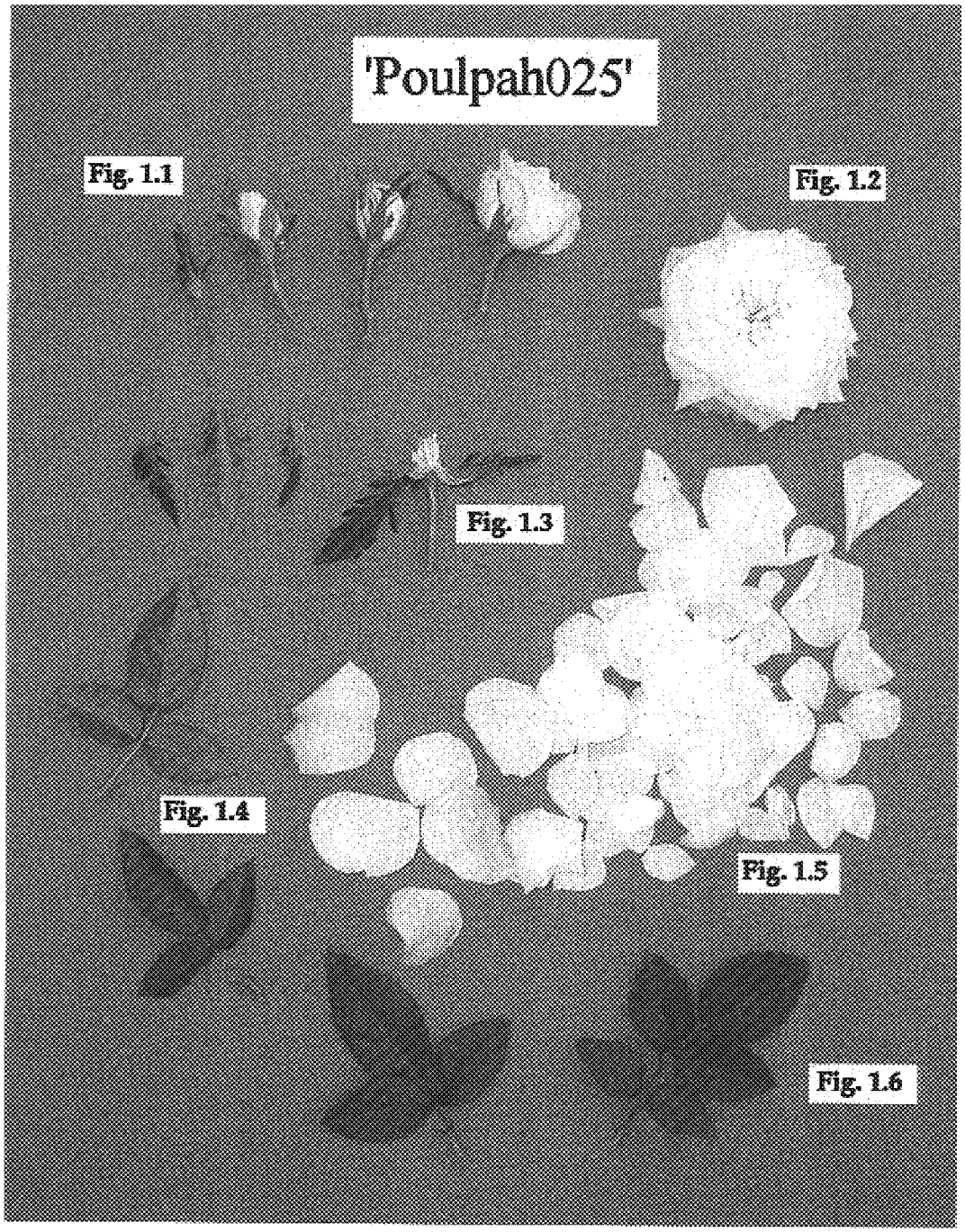
'Poulpah025'
Fig. 1.1
Fig. 1.2
Fig. 1.3
Fig. 1.4
Fig. 1.5
Fig. 1.6